United States Patent [19]

Gindler

[11] 4,115,064

[45] Sep. 19, 1978

[54] METHOD FOR BILIRUBIN DETERMINATION

[75] Inventor: E. Melvin Gindler, Rockford, Ill.

[73] Assignee: Pierce Chemical Company, Rockford, Ill.

[21] Appl. No.: 852,718

[22] Filed: Nov. 18, 1977

Related U.S. Application Data

[63] Continuation of Ser. No. 765,960, Feb. 7, 1977, abandoned.

[51] Int. Cl.² .............................................. G01N 33/16
[52] U.S. Cl. ................................................... 23/230 B
[58] Field of Search ....................................... 23/230 B

[56] References Cited

U.S. PATENT DOCUMENTS 3,652,222  3/1972  Denney et al. ..................... 23/230 B
3,853,476  12/1974  Rittersdorf et al. ........... 23/230 B X Primary Examiner—Robert M. Reese

[57] ABSTRACT

A combination of hydrazine and a hydrazide is used to destroy residual diazotized sulfanilic acid in the Jendrassik and Grof procedure for determining bilirubin glucuronide.

9 Claims, No Drawings

METHOD FOR BILIRUBIN DETERMINATION

This is a continuation of application Ser. No. 765,960, filed Feb. 7, 1977, now abandoned.

The present invention relates to the determination of bilirubin in biological fluids and, more particularly, to the quantitative spectrophotometric or colorimetric determination of bilirubin.

U.S. Pat. No. 3,652,222, issued on March 28, 1972, to Denney and Denney presents a comprehensive historical discussion of the manners in which bilirubin has been determined in biological fluids such as blood serum. An even more current survey is presented by Richard J. Henry et al. in the second edition of *Clinical Chemistry,* Principles and Techniques, Harper and Row, 1974, pp. 1037–1065. What is apparent from these surveys is that the Jendrassik and Grof procedure for determining bilirubin is very desirable. This procedure involves the formation of the azobilirubin complex under acid conditions and then transforming the red complex to its blue form by elevating the pH. Spectrophotometric measurements are made at the higher pH since, with the blue color, a wave length (600 nm) is used at which interference from natural colorants, such as carotene, is minimized.

As conventionally practiced, formation of the azobilirubin complex is effected by reacting bilirubin with diazotized sulfanilic acid, a p-sulfophenyl diazonium salt, in dilute HCl. The diazonium salt is prepared by reacting sodium nitrite with sulfanilic acid and, because the salt is recognized as being unstable, it is necessary to prepare the salt immediately to a day or two days before use.

Bilirubin in human blood serum exists largely in two forms, free bilirubin and bilirubin glucuronide. While both of these forms of bilirubin react with diazotized sulfanilic acid at high pH, only the latter, i.e., the glucuronide, reacts with the sulfanilic acid in dilute HCl. Therefore, in order to measure both the total bilirubin, i.e., the free bilirubin plus bilirubin glucuronide, and the direct reacting bilirubin, i.e., the glucuronide, it is conventional practice to run two measurements. A total bilirubin measurement is made on the sample wherein the diazotized sulfanilic acid is permitted to react with all the bilirubin present and a second measurement is made wherein the sulfanilic acid is only permitted to react with the bilirubin glucuronide present. The difference between the two measurements indicates the amount of free bilirubin in the sample.

In order to accomplish the second measurement, i.e., the bilirubin glucuronide, it is conventional practice to destroy the residual diazotized sulfanilic acid reacted with the sample in dilute HCl before the pH of the sample is elevated so as to give the blue azobilirubin color. The purpose of this destruction of residual diazonium salt is the prevention of unwanted subsequent coupling of free bilirubin with diazonium salt at higher pH. To this end, various agents have been added to the sample used for determining bilirubin glucuronide prior to the time at which the pH is raised. For a number of years, ascorbic acid was used as such an agent. The above referenced Denney and Denney patent discloses the use of hydroxylamine hydrochloride as a useful agent.

In accordance with the Denney and Denney patent, the use of hydroxylamine hydrochloride is stated as providing multiple advantages which include (a) blocking the reaction of bilirubin after a certain stage of the assay so that it is possible to distinguish the measurement of conjugated and unconjugated bilirubin, (b) prevention of interference of substances contained in erythrocytes in the assay, thus, for example, suppressing the interference of hemolysis of the assay, and (c) stabilizing the azobilirubin color formed in the reaction, making less critical the time of the observation. It is further stated that these advantages are realized without the instability of the ascorbic acid which was formerly used to achieve these goals. The abilities of both ascorbic acid and hydroxylamine salts to stabilize dyes in aqueous solutions have been known and used for many years.

Accordingly, it is a principal object of the present invention to provide a new method for determining bilirubin which has the advantages associated with the use of hydroxylamine hydrochloride. A further object resides in providing a method for bilirubin determination having these desirable attributes which involves the use of an improved system which enhances sensitivity of the determination. Related thereto is the additional object of providing a procedure for determining bilirubin wherein, due to enhanced sensitivity, only small samples of biological fluid need be employed.

Other objects and advantages of the present invention will become apparent upon reading the following detailed description. And, while the present invention will be described in connection with certain preferred embodiments, it is to be understood that the invention is not to be limited to only those embodiments illustrated. On the contrary, it is intended to cover all alternative and equivalent embodiments as may be included in the appended claims.

Now, in accordance with the present invention, it has been discovered that a combination of hydrazine and a hydrazide can be used for the destruction of residual diazotized sulfanilic acid in the determination of bilirubin glucuronide. While the use of these compounds is particularly applicable with respect to the Jendrassik and Grof method of determining bilirubin, it is also applicable with respect to any method of determining bilirubin wherein residual diazonium salt needs to be destroyed in order to obtain accuracy.

The compounds useful in the present invention can be represented as having the following structural formula:

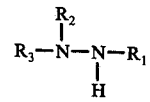

as well as hydrates thereof.

For hydrazine, all of the R groups are a hydrogen atom. For the hydrazides at least one of the R groups is other than a hydrogen atom and can be any radical which does not contain groups capable of reacting with diazonium salts to form colored complexes nor render the compound insoluble in water. Accordingly, the R groups can, for example, be carbonyl, sulfonyl, thiocarbonyl, alkyl, aryl and groups containing combinations of these radicals. The R groups can all be the same or they can be different. In general, to provide water solubility, no single R group will contain more than about 12 carbon atoms. The R groups, however, cannot include parts which form colored complexes with diazonium salts. Accordingly, excluded are ring structures containing conjugated unsaturation which are rendered reactive toward diazonium salts by the presence of electron donating groups on the ring. Therefore, excluded are compounds containing aromatic groups with substituents such as hydroxyl, amino, and sulfhydryl radicals.

Preferred hydrazides for use herein are those wherein $R_2$ and $R_3$ are H and wherein $R_1$ is

with Y being alkyl, amino, alkylamino, aryl, and alkylaryl. Particularly useful compounds of this type are acetythydrazide (Y is —$CH_3$), semicarbazide (Y is —$NH_2$) and its hydrochloride

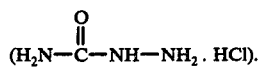

Benzhydrazide ($R_1$ is —$C_6H_5$ and $R_2$ and $R_3$ are H) is also useful. Other useful compounds include those hydrazides having the following structures:

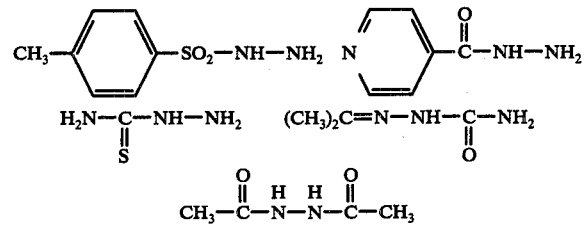

The present invention is best utilized in connection with the conventional Jendrassik and Grof procedure wherein the combination of hydrazine and a hydrazide is substituted for either ascorbic acid or hydroxylamine hydrochloride, as the case may be. Thus, except for the use of a different system, the manner of determining bilirubin can be the same as those conventionally practiced which involves preparing two samples, one being for the direct bilirubin determination and the other being for the total determination. As to the total determination, a total bilirubin accelerator such as a caffeine or dyphylline reagent solution is first added followed by addition of the diazotized sulfanilic acid color reagent. After sufficient time has elapsed to insure that all of the bilirubin has reacted with the color reagent, the combination of hydrazine and a hydrazide, in solution, can be added and thereafter the solution rendered alkaline by the addition of base. The direct determination can be made in a similar fashion except that in place of the total bilirubin accelerator, dilute hydrochloric acid is used. In addition, in order to insure that free bilirubin does not react with the color reagent, the hydrazine/hydrazide solution is added some minutes after the addition of the color reagent. Spectrophotometric measurements on both solutions can be made at about 600 nm and the quantitative measurement of direct and total bilirubin determined in conventional fashion from appropriate constructed calibration graphs or the like.

In general, the hydrazine and hydrazide are used in molar ratio, one to the other, of about 3:1 to 1:2, respectively, and, preferably, about 2.2:1 to 1.8:1. The total concentrations used of the combined compounds is about 0.1 to 0.7 mMol per 0.2 ml of sample and, preferable 0.3 to 0.5 mMol. per 0.2 ml of sample.

The following example illustrates the present invention.

EXAMPLE

The following solutions were prepared:

The Hydrazine/Hydrazide Solution

In situ preparation is preferred. Thus, in a 500-ml volumetric flask there is placed 62.5 ml anhydrous hydrazine, 125 ml isopropanol and 62.5 ml ethyl acetate. A clear solution results on gentle mixing, which is allowed to stand undisturbed at room temperature for two hours. It is then heated, with stirring, on a hot plate in a hood, with gentle refluxing, for one hour. Deionized water is added to give about 450 ml of solution. Then 1.00 gm of ethylenediaminetetraacetic acid is added (as the free acid to stabilize the solution against oxidation due to the presence of metal ions) and dissolved by stirring at room temperature. Deionized water is added, with good stirring, to give 500 ml of solution. The solution contains both hydrazine and acetylhydrazide.

Sulfanilic Acid Reagent

One liter of this solution in deionized water contains:
5.0 grams (26.15 mMol) p-sulfanilic acid monohydrate
60 ml (720 mMol) 12M (conc.) HCl Sodium Nitrite Solution One hundred milliliters of this solution in deionized water contains:
20.0 grams (0.2898) $NaNO_2$
0.090 grams Tetrasodium salt of ethylenediaminetetraacetic acid, dihydrate Total Bilirubin Accelerator:
500 ml of this solution in deionized water contains:
25.0 grams 7-(2,3-dihydoxpropyl)-theophylline, 99%
62.5 grams Sodium Acetate Trihydrate Alkaline Reagent: (to be protected from air)

In a 500-ml volumetric flask there is placed 55.3 gm (400 mMol.) analytical reagent grade Salicyclic Acid and about 200 ml of deionized water. 3.0 gm disodium salt of ethylenediaminetetraacetic acid (dihydrate) is then added. While stirring there is added 45 ml of 19.4 M sodium hydroxide solution. Then 50 ml of 23 mole ethyleneoxide adduct of lauryl alcohol (24% solution) is added and diluted to a total volume of 500 ml solution with deionized water. It is then filtered through Whatman Number 54 filter paper.

Color Reagent:

This reagent is prepared by mixing 250 volumes of the sulfanilic acid reagent with 1 volume of the sodium nitrite reagent. The color reagent is to be used within two hours of its preparation.

Direct bilirubin is measured by placing 0.200 ml of biological fluid sample, e.g., serum, in a 13 × 100 mm glass test tube followed by the addition of 2.00 ml of 0.05 M HCl and 0.100 ml color reagent. Exactly 7.0 minutes after the addition of the color reagent, 0.100 ml of hydrazine/hydrazide solution is added. After mixing, 1.0 ml of the alkaline reagent is added and the absorbance is then read at 600 nm.

For total bilirubin, 0.200 ml of sample is also placed in a 13 × 100 mm glass test tube. Then 2.00 ml of the total bilirubin accelerator is added followed by the addition of 0.100 ml color reagent. After 7 minutes, 0.100 ml hydrazine/hydrazide solution is added followed by the addition of alkaline reagent and spectrophotometric measurement as described with respect to the direct bilirubin.

A blank is run for each procedure by substituting sulfanilic acid solution for the color reagent. This blank absorbance is subtracted from the corresponding absorbance of the tube containing the color reagent as a correction for extraneous colored substances.

I claim:

1. In the method for determining bilirubin glucuronide in a sample containing both free bilirubin and bilirubin glucuronide comprising reacting the bilirubin glucuronide with diazotized sulfanilic acid to form a complex at a pH where said free bilirubin does not react with said acid, destroying any residual diazotized sulfanilic acid, and raising the pH so that colorimetric or spectrophotometric measurement of the complex can be achieved with minimization of interference from natural colorants; the improvement wherein there is used for the purpose of destroying the residual diazotized sulfanilic acid a combination of hydrazine and hydrazide.

2. The method of claim 1 wherein the hydrazide has the following structure:

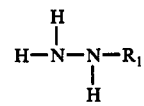

where $R_1$ is

containing not more than about 12 carbon atoms with Y being a group selected from alkyl, amino alkylamino, aryl or alkylaryl.

3. The method of claim 1 wherein the hydrazide is acetylhydrazide, semicarbazide, semicarbazide hydrochloride or benhydrazide.

4. The method of claim 1 wherein the hydrazide is acetylhydrazide.

5. The method of claim 1 wherein the molar ratio of hydrazine to hydrazide is between about 3:1 and 1:2.

6. The method of claim 4 wherein the molar ratio of hydrazine to acetylhydrazide is between about 2.2:1 and 1.8:1.

7. The method of claim 3 wherein the molar ratio of hydrazine to hydrazide is between about 3:1 and 1:2.

8. The method of claim 5 wherein, per 0.2 ml of sample, the total concentration of hydrazine and hydrazide is about 0.1 to 0.7 mMol.

9. The method of claim 6 wherein, per 0.2 ml of sample, the total concentration of hydrazine and acetylhydrazide is about 0.3 to 0.5 mMol.

* * * * *